United States Patent [19]
Brede

[11] Patent Number: 5,977,450
[45] Date of Patent: Nov. 2, 1999

[54] TURFGRASS CULTIVARS OF *ZOYSIA SINICA*

[75] Inventor: Andrew Douglas Brede, Veradale, Wash.

[73] Assignee: Jacklin Seed Company, Post Falls, Id.

[21] Appl. No.: 08/840,840

[22] Filed: Apr. 17, 1997

[51] Int. Cl.⁶ .............................. A01H 5/00; A01H 5/10; A01H 1/04
[52] U.S. Cl. .......................... 800/320; 800/298; 800/360; Plt./388; Plt./390
[58] Field of Search ..................................... 800/200, 230, 800/235, 250, DIG. 55, 278, 320, 360; 435/430; 47/58, DIG. 1; Plt./388, 390

[56] References Cited

PUBLICATIONS

Hong et al. Studies on interspecific hybridization in Korean lawn grasses (Zoysia spp.) Journal of the Korean Society for Horticultural Science, vol. 26, pp. 169–178, 1985.

*Primary Examiner*—Lynette R. F. Smith
*Assistant Examiner*—Melissa L. Kimball
*Attorney, Agent, or Firm*—Rothwell, Figg, Ernst & Kurz

[57] ABSTRACT

A *Zoysia sinica* turfgrass variety is disclosed. The invention relates to the seeds, the plants, and to methods for producing a Zoysia plant having the characteristic of a seedhead density of greater than zero.

10 Claims, No Drawings

TURFGRASS CULTIVARS OF *ZOYSIA SINICA*

This invention relates to the production of new turfgrass cultivars of seashore zoysiagrass (*Zoysia sinica* Hance), an obscure grass species that has never before been commercially developed as turfgrass. Cultivars produced by selective breeding from this species offer advantages in plant density, disease resistance, and turf quality over genetic plant material found in nature.

BACKGROUND

Homeowners and turfgrass managers in the United States rely on fewer than 20 plant species for all their grassing needs. Moreover, nearly all of these 20 grasses originate from the same general region of Eurasia. An estimated 46.5 million acres of turfgrasses are presently grown in the US (*Grounds Maintenance* magazine, May 1996, p. 10.). Concentrating this few number of species over a vast agricultural landscape is bound to produce problems over time as disease or insect organisms build up and become virulent against existing grasses. This type of pandemic actually occurred in the US in recent years, when large acres of the corn belt were decimated by an outbreak of southern corn leaf blight when a mutated strain of the disease arose.

The solution to this dilemma lies in species diversity. Agriculturists have found that by increasing the number and breadth of species, there is increased genetic diversity and less chance that a particular parasite will devastate a substantial acreage of plants.

Another factor urgently needed is diversity in where species originate. Most of the common turfgrasses grown in this country—Kentucky bluegrass (*Poa pratensis* L.), creeping bentgrass (*Agrostis stolonifera* L.), fine fescue (Festuca spp.), tall fescue (*F. arundinacea* Schreb.), and perennial ryegrass (*Lolium perenne* L.)—species that comprise the bulk of turf in the temperate zone—derive from the same region of Europe. Only one turfgrass species originates from here in North America (*Buchloe dactyloides* [Nutt.] Engelm.) and only two from Eastern Asia (*Zoysia japonica* Willd. and *Eremochloa ophiuroides* [Munro.] Hack). To increase the breadth of genetic origin, more turfgrasses are needed that originate from a broader sector of world geography, to bolster the diversity of today's turfgrasses.

Another advantage of seeking out additional turf species is to help reduce turf maintenance levels. Present-day turfgrasses are better suited to high maintenance than low. They perform best when given a steady diet of water, fertilizer, and chemical pesticides. In theory, grasses native to a particular locale should be able to withstand local growing conditions better than exotics, without the need for additives and preservatives. Grass species that can survive on less input of water or other scarce natural resources offer benefits for reducing maintenance and improving environmental friendliness of lawns.

But finding and developing new grass species from nature is difficult, time consuming, and expensive. The developer must sift through thousands of prospective grasses listed in botanical literature, identify promising grasses, and travel thousands of miles to locate, isolate, identify, transport, quarantine, grow, test, and breed these grasses. This process can take more than 10 years to develop acceptable cultivars. Furthermore, as it turns out, most prospective grasses in nature have no commercial turf value, due to their inability to generate an acceptable ground cover when mowed. The vast majority of natural grasses cannot produce a plush lawn under continuing defoliation.

Also, few grasses found in nature have the ability to produce marketable quantities of seed—a critical necessity for commercialization of a new grass species. Raw germplasm of most native grasses seldom tops 100 lbs. per acre in seed production (R. S. Sadasivaiah and J. Weijer, 1981, The utilization of native grass species for reclamation of disturbed land in the alpine and subalpine regions of Alberta. In Reclamation in mountainous areas. Proc. 6th ann. meeting Can. Land Reclam. Assoc.); this level of production is not high enough for economic viability. By contrast, popular grasses like tall fescue have been cultivated and selected since prehistoric times for cattle fodder. Only high yielding plant lines have persisted through the ages. Many of today's tall fescue cultivars top 1 ton per acre in seed production.

Yet another complexity facing the plant developer is the unresponsiveness of many wild grasses to plant breeding. The vast majority of wildland grasses lack genetic potential for refinement into desirable turfgrass cultivars. Only after considerable investment in collection and breeding does the developer discover which grass species can be successful bred and which cannot.

Eastern China is the center of origin for three zoysia species: *Z. japonica, Z. sinica,* and *Z. macrostachya. Zoysia japonica*, commonly known as Japanese zoysia, is a popular turfgrass in the Asia Pacific Rim countries and in the US mid-Atlantic region. Several vegetatively propagated cultivars have been developed from this species, including 'Meyer,' 'El Toro,' 'Belair,' and 'Midwest.' All of these cultivars are clonally propagated by means of vegetative cuttings. Only in recent years has there been effort to develop seeded cultivars of *Z. japonica*, due to the fact that breeding of the species is slow and tedious (S. H. Samudio, 1996, Whatever became of the improved seeded zoysia varieties? *Golf Course Mgmt.* August 1996, p. 57–60). Only two seeded *Z. japonica* cultivars, 'W3-2' and 'Zenith,' have been sold commercially.

To date, *Zoysia sinica* Hance and *Zoysia macrostachya* Franch. et Sav. have never been commercially developed. In China and its neighboring countries, these two grasses are native to the seashore. They are found along coastal plains with seawater often washing their roots. Scientists have speculated that these two grasses may be halophytes—plants that actually require salt as part of their metabolism (K. B. Marcum, M. C. Engelke, and S. J. Morton, 1993, Salt tolerance and associated salt gland activity of zoysiagrasses, Agronomy Abstr., Amer. Soc. Of Agronomy, Madison, Wis.). Hence, these species hold the potential for soil stabilization in areas of high salt soils or saline irrigation water. More and more, salt intrusion is becoming a concern in many areas of the US, including Florida, Texas, and most of the West.

*Zoysia sinica* has no common (English) name. Therefore, the name "seashore zoysiagrass" is proposed for this species to designate its seaside origins.

Vegetatively, seashore zoysiagrass is quite similar in appearance to Japanese zoysia. The main differentiating point is seed length. Seed of *Z. sinica* are about twice as long as those of *Z. japonica*, making identification possible even with a single seed.

Quantities of Chinese common zoysia seed have been produced and imported into the US in recent years. While most of this seed is *Z. japonica*, a minute amount is *Z. sinica* and *Z. macrostachya*. Chinese zoysia seed is hand-harvested in the wilds, throughout mountains and along the seashore. Although the harvesters are pursuing the much-sought-after *Z. japonica* seed, they sometimes inadvertently harvest patches of *Z. sinica* or *Z. macrostachya*. Hence, a small amount of *Z. sinica* makes its way into this country each year, albeit incognito.

Dong and Chen (L. S. Dong and B. X. Chen, 1991, Zoysia germplasm resource investigation in the Jiaozhou Bay, Qingdao Lawn Construction Development Co., Qingdao, Shandong, PRC) characterize *Z. sinica* as:

Root-shaped creeping stems, and height of 7–15 cm, thread-shaped coniferous leaves with hard textures and a length of 3–7 cm and a width of 3 mm. The leaf edges bent inward with long soft hairs around the leaf sheath, the ligule is a circle with long soft hairs, the total ear length is 3–4 cm and the width, 2 mm. The spikelet is light purple with a length of 3–4 cm and a width of 1.5 mm and coniferous leaves. The stem of the spikelet is 1–2 mm. The blooming stage is May–July and the seed-setting time is July–August.

In Korea, Hong et al. (K. Hong, H. Yeam, and Y. Do, 1985, Studies on interspecific hybridization in Korean lawngrass [Zoysia spp.], *J. Korean Soc. of Hort. Sci.* 26(2):169–178) describe *Z. sinica* as being taller growing than *Z. japonica*. And they found differences between the two species in their natural occurrence. They describe the indigenous habitat of *Z. japonica* as inland "fields," versus the habitat of *Z. sinica* as the "slime along the shore." Hong et al. characterized the average seed length of *Z. sinica* as 5.3 mm, compared to 2.4 mm for *Z. japonica*. The leaf width of *Z. sinica* was a finer 2.9 mm, versus 5.1 mm for *Z. japonica*. They found that *Z. sinica* was capable of producing viable seed when pollinated with *Z. macrostachya*, suggesting a genetic connection between the two species.

SUMMARY OF THE INVENTION

The present invention provides for the development of novel cultivars of an obscure grass species never before exploited for turf purposes. Cultivars developed from this species demonstrate enhanced turfgrass properties, as demonstrated in the section to follow, including improvements in mite tolerance, shoot density, fineness of leaf, and overall turfgrass quality.

More specifically, the present invention relates to a *Zoysia sinica* plant having the characteristics of an average seedhead density of greater than zero.

The present invention further relates to a *Zoysia sinica* plant having an average shoot density of greater than 0.56 shoots per cm$^2$.

The invention further relates to a method of making an $F_1$ hybrid by crossing the plant of the present invention with another *Zoysia sinica* plant.

DETAILED DESCRIPTION OF THE INVENTION

Definitions

In the description and tables which follow, a number of terms are used. In order to provide a clear and consistent understanding of the specification and claims, including the scope to be given such terms, the following definitions are provided:

Average Shoot Density: As used herein, the term average shoot density means the number of grass shoots measured in four plugs. During the process of blade width measurement, the number of grass shoots for each genotype are counted in the four plugs of a 2 inch×5 inch area. A grass shoot is defined as an autonomous unit possessing a vertical sheath segment, and a minimum of two leaves, including the vertical or bud leaf. Shoot counts per plug are converted numerically into shoots per cm$^2$, based on the exact measured area of the plug.

Leaf Color: The term leaf color means the leaf color is evaluated visually on a 1 to 9 integer rating scale, in a manner similar to turfgrass quality. With leaf color evaluation, a rating of 1 would equate to yellow-green turf, 5 to average green turf, and 9 to intensely dark green turf color. Ratings are taken when the turf is actively growing, when regular mowing is taking place, and when no stresses such as drought or disease are apparent.

Seedhead Density: The term seedhead density refers to the relative number of seedheads (inflorescences) expressed under controlled, unmowed conditions. After seedheads, also called inflorescences, protrude, the plants are evaluated on a visual rating scale of 1 to 9, with 1 equal to no visible heads, 5 equal to an average number of seedheads, and 9 equal to an exceptionally high number of seedheads. An analysis of variance is used for differentiating replicates of like plants, using the same type of analysis as for turf quality.

Significant Difference: As used in the tables, the indication of "*", "*", and "**" asterisks indicate significant differences at the $p \leq 0.05$, 0.01, and 0.001 levels, respectively.

Stolon Internode Length: The term stolon internode length defines plants that are established in an unclipped, bare-ground, spaced plant nursery, using greenhouse-grown, vegetatively potted plants of at least 6 months of age. The field plants are grown for 3 summer months in a location climatologically similar to Post Falls, Idaho (where the data in this experiment were collected). Stolons (lateral, surface-creeping stems) are permitted to naturally grow. The length of the stolon internode is measured as the distance between two successive nodes once the stolon reaches a length of at least 4 inches. The measurement is taken between the 3rd and 4th nodes, counted inward from the apex of the stolon. Readings are taken in millimeters from the center of one node to the next.

Turfgrass Quality: The term turfgrass quality is determined in the following manner: Grasses are seeded into plots 4 feet×6 feet or 5 feet by 5 feet at a seeding rate (seed grams per square meter) equal to commercial rates listed in turf textbooks. Plots are maintained under fertilization and watering to minimize stress, and at a weekly mowing height of ¾ inch to 1½ inch. Four plots of Variety A are planted in a randomized complete block design arrangement with four plots of Variety B. Visual ratings are taken monthly during the growing season on a 1 to 9 rating scale, with 1 equal to bare ground, 2 equal to thin, brown turf, 3 equal to substandard turf, 4 equal to marginally acceptable turf, 5 equal to average turf, 6 equal to slightly above average turf, 7 equal to dense, robust turf, 8 equal to turf of exceptional quality, and 9 equal to ideal turf quality. Only integer values are recorded. Ratings are conducted by a university-trained specialist with a graduate degree in Turfgrass Science. Monthly data ratings are analyzed using a statistical procedure known as the analysis of variance and either a t-test or LSD test, at the 0.05 level of probability. A significant analysis indicates the two varieties, A and B, are different, and that the difference is not due to random error or natural plant and soil variability. A non-significant analysis would indicate that the varieties A and B were indistinguishable in turf quality and could be considered to be identical.

Vegetative propagules: As used herein, the term vegetative propagules means sprigs, plugs, stolons and sod.

Yield Estimate: As used herein the term yield estimate is determined on plants which are grown as previously described for "seedhead density." Yield ratings are based on a combination of factors, including the seedhead density, reproductive length of the seedhead, width of the seedhead. Ratings are based on a 1 to 9 scale with 1 equaling no yield productivity, 5 equaling average productivity, and 9 equaling exceptionally high productivity. An analysis of variance is used for differentiating replicates of like plants, using the same type of analysis as for turf quality.

The novel turfgrass cultivars developed by this invention may be produced by following the detailed descriptions listed below. The process began with identification of species with turfgrass potential through an exhaustive search of the botanical literature. Numerous promising grass species were identified, located, tested, and rejected before *Z. sinica* were entered into plant breeding. The plant breeding phase of this invention follows conventional breeding methods as outlined in a number of plant breeding textbooks, using a method called modified recurrent selection. The net result of their breeding is a series of cultivars with enhanced turfgrass performance. The improvements instilled into these cultivars are quantifiable and distinctive. Raw germplasm of these species from nature performs poorly as mowed turf, if it survives at all. The enhanced cultivars perform competitively with other popular turf cultivars.

Germplasm collection trips were mounted to Japan in 1987 and to China in 1990, 1991, and 1993 to bring seed of *Zoysia sinica* back for testing and development. Seed, as opposed to vegetative plant material, was brought into the US to avoid unnecessary quarantine delays. Introduction of seed also avoided the problem of unwittingly importing a virus or insect along with the germplasm.

Following quarantine inspection, imported seed was sprouted in a greenhouse and transplanted to spaced-plant, field observation nurseries near Visalia, Calif., Phoenix, Ariz., Post Falls, Id., and Lakeland, Ga. The latter site proved most satisfactory for propagating and breeding seashore zoysiagrass.

J-14, an improved *Z. sinica* cultivar, was assembled from superior seashore zoysiagrass clones planted in nurseries near Lakeland, Ga., in 1991 and 1993. During the spring of 1994, 36 clones were moved to an isolated crossing block labeled, 94-0014. Plants were individually harvested in June, 1994. Seed was treated and germination was tested: 16 lines were dropped based on poor germination. Seed from the remaining 20 lines was used to plant a 1200-plant breeder block in August, 1994. In 1995, the plants were still relatively small, but several clones were discarded to increase uniformity; coarse textured, light green, and bluish plants were removed.

During 1996, we determined that some of the lines were actually *Z. sinica*×*Z. japonica* interspecific hybrids. These plants were rogued from the breeder block. First breeder seed will be produced in 1997; commercial seed should be available by 1999.

Visual ratings and botanical measurements were taken from the J-14 cultivar and from various unimproved seashore zoysiagrass plants in the nurseries which are plants derived directly from nature without breeding intervention. Data were analyzed using analysis of variance and unpaired t-tests to determine statistical differences between the groups as shown in Tables 1 and 2. The genetic improvements in *Z. sinica* instilled by the breeder are: 1) Improved seedhead density and seed yielding ability with 2) enhanced turfgrass quality which is a function of the visual attractiveness of the turf; a composite of disease and insect resistance, vigor, density, color, and growth habit, 3) higher shoot density in mowed turf; and 4) a shorter stolon internode length (indicating the plants were better adapted for dense turf conditions).

In Table 1, data is shown on J-14, an improved seashore zoysia (*Zoysia sinica* Hance) cultivar versus unimproved, raw germplasm collected from nature (Qingdao, China). This spaced-plant nursery near Lakeland, Ga., was planted in May, 1993, and was evaluated through April, 1996.

The common *Z. sinica* in this table represents means from several sources originating from seed of unimproved *Z. sinica* landraces collected near Qingdao, China. Unimproved germplasm sources include: 92-124-1, 92-124-2, 92-124-3, 92-124-4, 92-124-6, 92-124-7, 92-125-1, 92-125-2, 92-125-3, 92-127-1, 92-128-1, 92-128-2, 92-128-3, 92-130-1, 92-130-2, 92-132-1, 92-132-2, 92-132-3, 92-132-4, 92-132-5, 92-133-1, 92-133-2, 92-134-1, 92-134-10, 92-134-11, 92-134-2, 92-134-3, 92-134-4, 92-134-5, 92-134-6, 92-134-7, 92-134-8, 92-134-9, 92-135-1, 92-135-10, 92-135-11, 92-135-12, 92-135-13, 92-135-14, 92-135-15, 92-135-16, 92-135-17, 92-135-18, 92-135-9, 92-135-2, 92-135-20, 92-135-21, 92-135-22, 92-135-23, 92-135-24, 92-135-25, 92-135-26, 92-135-27, 92-135-28, 92-135-29, 92-135-3, 92-135-30, 92-135-31, 92-135-32, 92-135-33, 92-135-34, 92-135-35, 92-135-36, 92-135-37, 92-135-38, 92-135-39, 92-135-4, 92-135-40, 92-135-41, 92-135-42, 92-135-43, 92-135-44, 92-135-45, 92-135-46, 92-135-47, 92-135-48, 92-135-49, 92- 135-5, 92-135-50, 92-135-51, 92-135-52, 92-135-53, 92-135-54, 92-135-54, 92-135-55, 92-135-56, 92-135-57, 92-135-58, 92-135-59, 92-135-6, 92-135-60, 92-135-61, 92-135-62, 92-135-63, 92-135-64, 92-135-65, 92-135-66, 92-135-67, 92-135-68, 92-135-69, 92-135-7, 92-135-70, 92-135-71, 92-135-72, 92-135-73, 92-135-74, 92-135-75, 92-135-76, 92-135-77, 92-135-78, 92-135-79, 92-135-8, 92-135-80, 92-135-81, 92-135-82, 92-135-83, 92-135-84, 92-135-85, 92-135-86, 92-135-87, 92-135-88, 92-135-89, 92-135-9, 92-135-90, 92-135-91, 92-135-92, 92-135-93, 92-135-94, 92-135-95, 92-135-96, 92-137-1, 92-137-2, 92-137-3, 92-137-4, 92-138-1, 92-138-10, 92-138-11, 92-138-12, 92-138-13, 92-138-2, 92-138-3, 92-138-4, 92-138-5, 92-138-6, 92-138-7, 92-138-8, and 92-139-1.

J-14 was bred from sources collected near Qingdao, China and Centerville, Tenn., including: 91-34, 92-95-3, 92-101-2, 92-108-17, 92-110-10, 92-110-13, 92-110-2, 92-111-1, 92-113-17, 92-120-21, 92-120-22, 92-120-31, 92-120-32, 92-120-8, 92-122-3, 92-123-13, 92-124-5, and 92-138-14.

Visual ratings were based on a 1 to 9 scale where 9=best turf quality, finest leaves, highest yield (based on a combination of number of seedheads per plant and the length of the seedheads), or most seedheads per plant.

TABLE 1

| Group† | Seedhead density April 96 | Yield estimate April 96 | Leaf texture March 96 | Turfgrass quality October 93 |
|---|---|---|---|---|
| J-14 *Zoysia sinica* | 6.6 | 4.4 | 5.4 | 5.4 |
| Common *Z. sinica* | 4.4*** | 2.9** | 5.8* | 3.9** |

In Table 2, morphological evaluations of J-14, an improved seashore zoysia (*Zoysia sinica* Hance) cultivar are shown versus unimproved, common *Z. sinica* landraces from China. Common *Z. japonica* grown in China from landraces is also included as a reference standard. Plants in this trial were established in Post Falls, Id., as 6-inch plugs in June, 1996; measurements were taken September, 1996. Natural height was measured as the freestanding height of plants without seedheads. Stolon internode length was measured between nodes 3 and 4 from the meristem.

TABLE 2

| Group† | Natural vegetation height (mm) | Stolon internode (mm) |
| --- | --- | --- |
| J-14 Z. sinica | 144 | 27 |
| Common Z. sinica | 111* | 34* |
| Sunrise® brand Chinese common | 101* | 38* |

Morphological evaluations of improved Zoysia sinica Hance versus unimproved wild-type Z. sinica are shown in Table 3. Plants in this trial originated from individual sprigs, planted in the field in Post Falls, Id. in June, 1996. Plants were grown through the summer and fall, and on Oct. 10, 1996, 1 inch diameter plugs were removed and planted into 6 inch (15 cm) Promix-filled pots in the greenhouse. The greenhouse air temperature was maintained at an average of 68° F. during the day and 55° F. at night. Soil in the pots was continually warmed to 70° F. using underneath, hot-water heating. Air relative humidity was 55%. Daylight and photoperiod were supplemented with artificial sodium light from 3:45 p.m. to 10:00 p.m. daily. Pots were watered once a day by mist for two minutes. Fertilization was 2.7 lbs. Nitrogen per 1000 ft$^2$ from Peter's 20-20-20 once a month, and 2 lbs nitrogen per 1000 ft$^2$ from PFC 18-10-10-7 every three weeks. Plants were not clipped. Measurements were taken Feb. 10, 1997. Statistical differences were based on a total of 19 pots, with data analyzed using unpaired t-tests. Probabilities less than 0.05 are statistically significant.

As shown in Table 3, the average shoot density for the present invention was 0.72 versus the mean of 0.47 for previous Zoysia sinica germplasm. The present invention also had an average seedhead density of 22 and mite tolerance of 64 versus average seedhead density of 0 and mite tolerance of 95 for the unrefined Zoysia germplasm.

TABLE 3

| | Zoysia sinica Present Invention | | | | Zoysia sinica Unimproved | |
| --- | --- | --- | --- | --- | --- | --- |
| | Avg | Deviation | Standard Probability | n | Avg | Standard Deviation |
| Shoot density (shoots/cm$^2$) | 0.72 | 0.15 | .00024 | 19 | 0.47 | 0.09 |
| Seedhead density | 22 | 7 | .00000 | 19 | 0 | 0 |
| (influorescences per pot) Mite Tolerance (% of total leaves showing mite damage based on 10 leaves per pot | 64 | 16 | .00002 | 19 | 95 | 7 |
| Stolon count (perpot) | 1.8 | 1.6 | .00004 | 19 | 9.0 | 3.5 |

DEPOSIT INFORMATION

Zoysia sinica seed of this invention has been placed on deposit with the American Type Culture Collection (ATCC), Manassas, Va. 20110, under Deposit Accession Number, 97951 on Mar. 13, 1997.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An Zoysia sinica seed designated J-14, wherein a sample of said seed has been deposited with the American Type Culture Collection under ATCC Accession No. 97951.

2. The plant or its parts produced by the seed of claim 1.

3. Pollen of the plant of claim 2.

4. An ovule of the plant of claim 2.

5. Vegetative propagules of the plant of claim 2.

6. A Zoysia sinica plant having all of the physiological and morphological characteristics of the Zoysia sinica plant of claim 2.

7. A method for producing a hybrid Zoysia sinica seed comprising crossing a first parent Zoysia sinica plant with a second parent Zoysia sinica plant and harvesting the resultant hybrid Zoysia sinica seed, wherein said first or second parent Zoysia sinica plant is the Zoysia sinica plant of claim 2.

8. A hybrid seed produced by the method of claim 7.

9. A hybrid plant or its parts produced by growing said hybrid Zoysia sinica seed of claim 8.

10. Vegetative propagules of the plant of claim 9.

* * * * *